United States Patent
Kane et al.

(10) Patent No.: US 8,958,891 B2
(45) Date of Patent: Feb. 17, 2015

(54) REINFORCED SUTURE SLEEVE

(75) Inventors: Larry Kane, St. Paul, MN (US); Qingshan Ye, Plymouth, MN (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 12/833,061

(22) Filed: Jul. 9, 2010

(65) Prior Publication Data
US 2011/0009935 A1    Jan. 13, 2011

Related U.S. Application Data

(60) Provisional application No. 61/224,488, filed on Jul. 10, 2009.

(51) Int. Cl.
*A61N 1/00* (2006.01)
*A61N 1/05* (2006.01)

(52) U.S. Cl.
CPC  *A61N 1/05* (2013.01); *A61N 1/057* (2013.01); *A61N 1/0558* (2013.01); *A61N 1/059* (2013.01); *A61N 2001/0582* (2013.01)
USPC ........................... 607/126; 607/116; 607/132

(58) Field of Classification Search
CPC . A61N 1/059; A61N 2001/0582; A61N 1/05; A61N 1/057; A61N 1/0558; A61N 1/056; A61N 1/0551; A61M 2025/0286
USPC ........... 607/116, 126, 132; 604/175; 606/129, 606/151, 232
See application file for complete search history.

(56) References Cited

U.S. PATENT DOCUMENTS

| | | | |
|---|---|---|---|
| 4,287,891 A | 9/1981 | Peters | |
| 4,516,584 A | 5/1985 | Garcia | |
| 4,553,961 A * | 11/1985 | Pohndorf et al. | 604/175 |
| 5,107,856 A | 4/1992 | Kristiansen et al. | |
| 5,152,298 A | 10/1992 | Kreyenhagen et al. | |
| 5,242,431 A | 9/1993 | Kristiansen | |
| 5,423,763 A | 6/1995 | Helland et al. | |
| 5,584,874 A | 12/1996 | Rugland et al. | |
| 5,674,273 A | 10/1997 | Helland | |

(Continued)

FOREIGN PATENT DOCUMENTS

| | | |
|---|---|---|
| WO | 2005061047 | 7/2005 |
| WO | 2007024164 | 3/2007 |

OTHER PUBLICATIONS

Hong Li and John Helland, In Vitro Evaluation of New Design Lead Anchoring Sleeves, 1992.

(Continued)

*Primary Examiner* — Niketa Patel
*Assistant Examiner* — William Levicky
(74) *Attorney, Agent, or Firm* — Michael F. Scalise (57) ABSTRACT

A reinforced suture sleeve designed to cover and protect a medical lead from physical damage resulting from an over tightened suture is described. The reinforced suture sleeve comprises a metallic tubular insert with at least one slot that cut through the surface of the insert in a spiraled pattern. A biocompatible and pliable polymeric body is molded over the insert. The spiraled cut slot in the metallic tubular insert provides flexibility without degrading structural integrity. An alternate embodiment comprises a polymeric body provided with an embedded fiber mesh made of polymeric fibers, metallic fibers or combinations thereof. The fiber mesh prevents an over tightened suture from cutting through the suture sleeve and damaging the medical lead.

25 Claims, 6 Drawing Sheets

(56) References Cited

U.S. PATENT DOCUMENTS

| | | | |
|---|---|---|---|
| 5,897,504 A * | 4/1999 | Buck et al. | 600/463 |
| 5,957,968 A | 9/1999 | Belden et al. | |
| 7,082,337 B2 | 7/2006 | Sommer et al. | |
| 7,218,972 B2 | 5/2007 | Rodriguez | |
| 7,242,986 B2 | 7/2007 | Rodriguez | |
| 7,579,550 B2 * | 8/2009 | Dayton et al. | 174/108 |
| 2003/0050668 A1 | 3/2003 | Lee | |
| 2004/0199234 A1 | 10/2004 | Rodriguez | |
| 2004/0254623 A1 | 12/2004 | Rodriguez et al. | |
| 2005/0137664 A1 * | 6/2005 | Sommer et al. | 607/115 |
| 2007/0078399 A1 * | 4/2007 | Olson | 604/175 |
| 2007/0287955 A1 * | 12/2007 | Layman et al. | 604/93.01 |
| 2008/0009928 A1 * | 1/2008 | Osypka et al. | 607/116 |
| 2008/0057784 A1 * | 3/2008 | Zarembo et al. | 439/592 |

OTHER PUBLICATIONS

Invention Disclosure, Title of Invention: Reinforced Suture Sleeve, enpath medical inc, Oct. 2006.
Patentability Search—Suture Sleeve, Oct. 6, 2008.
European Search Report, 2010.

* cited by examiner

REINFORCED SUTURE SLEEVE

CROSS-REFERENCE TO RELATED APPLICATION

The present application claims priority from U.S. Provisional Application Ser. No. 61/224,488 filed Jul. 10, 2009.

BACKGROUND OF THE INVENTION

1. Field of the Invention

The present invention is related generally to implantable medical electrical leads. More specifically, the present invention is related to a suture sleeve for an implantable medical electrical lead.

2. Prior Art

Suture sleeves are devices that are intended to provide a means of safely and securely anchoring a medical lead inside the body. Typically, a suture sleeve is slid over a medical lead to a location where it is desired to anchor the lead inside the body. Once the sleeve is in place, sutures, which are typically stranded fibers, are wrapped around the sleeve. The sleeve is intended to provide a housing-like structure that surrounds the medical lead, preventing the suture material from contacting the lead that could potentially cause damage to the lead.

After the sleeve is secured to the lead, the suture sleeve is sewn into place in the surrounding body tissue, anchoring the lead in place. The suture sleeve, therefore, is designed to provide an anchoring structure for the lead while protecting the lead from potential damage during and after the implantation process.

One of the main problems with current suture sleeves is their lack of adequate protection from over tightened suture materials. If the sutures are tied too tight, there is an increased likelihood that the sutures could cut through the polymeric body of the sleeve and continue to cut into the lead, resulting in a damaged and impaired lead. If the suture material were to propagate through the sleeve body and further cut into the lead, the lead could possibly be fractured or even severed resulting in a malfunctioning lead. Such a damaged lead would require replacement which would add further unnecessary expense and trauma to the patient.

Suture sleeves are typically made from a biocompatible pliable polymer such as silicone rubber. This provides durability and flexibility to the sleeve and allows the suture sleeve to move with the lead during and after implantation. The silicone material is ideal for long term implantation due to its biocompatibility, flexibility, and durability properties but polymeric materials, such as silicone, are not an ideal barrier against preventing the suture strands from cutting through the silicone sleeve body and damaging the medical lead.

When the sutures are tied too tight, the suture strands cut into the polymeric sleeve material. Over time, the suture material begins to cut deeper into the sleeve, propagating through the sleeve creating cracks and splits under the stress of the tightly wound suture threads. This is especially true of silicone rubber, as once the material is cut, the slice easily propagates through the material. Eventually, the suture material propagates through the sleeve structure and begins to cut into the medical lead, destroying the anchoring structure and damaging the lead.

The reality of over tightened sutures is a major problem. There is currently no known means of controlling the force at which sutures are tightened. Every physician ties sutures with a different force every time. A suture could easily be over tightened during an emergency situation when the physician must act immediately without much thought of the force at which the sutures are tightened. Therefore, there is a need to improve the integrity of the suture sleeve to ensure that regardless of the force exerted on the suture sleeve, by the suture material, the lead is not damaged.

Rodriguez in U.S. Pat. No. 7,218,972, discusses a reinforced suture sleeve comprising a tubular body, sleeve wall and inner lumen. The tubular body is made of silicone rubber and comprises three circumferential grooves to facilitate wrapping the suture material around the outside surface of the sleeve. The sleeve wall has an inner lumen made of polyurethane which is intended to prevent an over tightened suture from cutting into the lead. According to Rodriguez, the purpose of the polyurethane inner lumen is to prevent the suture from propagating through the suture sleeve and cutting into the medical lead, thereby damaging the lead. However, such a polymeric inner lumen does not provide adequate protection from the cutting action of the suture material.

The present invention discloses a suture sleeve with reinforcement embodiments that provide superior protection from over tightened sutures while providing flexibility that enables the suture sleeve to bend and flex with the medical lead. The first reinforcement embodiment comprises a suture sleeve with an internal metallic insert that has a spiraled slot cut through its surface. The metallic insert acts as a barrier that prevents sutures from cutting into the medical lead and the spiraled slot gives the insert and resultant suture sleeve, much needed flexibility. A second reinforcement embodiment entails embedding a flexible fiber mesh into the polymeric body of the suture sleeve. The embedded fiber mesh acts as a barrier and prevents further propagation of the suture material into the sleeve while still providing flexibility to the sleeve. This embedded fiber mesh also prevents the suture material from contacting the metal insert. Therefore, the possibility that the suture material will become damaged or broken from abrading against the metal insert is reduced.

Rodriguez, unlike the present invention, does not disclose a metallic inner lumen with a spiral slot cut through the insert surface nor does Rodriguez disclose the use of a fabric mesh reinforcement embodiment that is incorporated in the sleeve body. The present invention provides increased flexibility, durability and medical lead protection that are not afforded by Rodriguez.

In a related U.S. patent application publication number 2004/0254623, Rodriquez discloses a similar suture sleeve as presented in the '972 patent, however, in this application, the polymeric sleeve insert has a variable inner wall thickness of differing geometries. As stated in the '623 application, the variable inner wall thickness is designed to provide protection from an over tightened suture as the differing geometries of the inner lumen wall compress together. The present invention, unlike Rodriguez's application, is directed to the incorporation of insert reinforcement barriers which prevent the suture material from initially cutting into the inner lumen.

Pohndorf et al. in U.S. Pat. No. 4,553,961 discloses a suture sleeve with a structure for enhancing the grip of the sleeve around the lead. The suture sleeve comprises a sleeve body made of a silicone material with a hollow passageway through the center. A cylindrical insert that provides enhanced gripping of the sleeve is molded into the center passageway of the sleeve. The inserts of various designs are intended to grip the outside surface of the lead body to prohibit movement of the sleeve along the lead.

Each of the embodiments of the cylindrical insert in the '961 patent contains horizontal slits that extend through the end of the insert. These slits as shown by Pohndorf do not provide flexibility and do not allow the sleeve to bend as provided by the sleeve reinforcement embodiments of the present invention. In addition, the slits disclosed in the '961 patent, in which the slits cut through the insert end, degrade the physical integrity of the insert, thus reducing the internal structural strength and barrier qualities of the suture sleeve.

Unlike the present invention, Pohndorf does not teach a metallic insert with a spiral slot cut through the surface of the insert. The spiral cut insert embodiment of the present invention provides a flexible barrier that stops propagation of the suture material through the suture sleeve. Pohndorf's insert embodiments lack the required structural integrity that is provided by the present invention.

Helland in U.S. Pat. No. 5,674,273 discloses an implantable pacing lead with a reinforcing sheath covering a portion of the lead body. The sheath covering is designed to prevent damage to the lead due to tightly wound sutures that cut through the sleeve body.

Helland discloses a fixture sheath comprising a spiral wound flat wire that is encased within a layer of polymer covering that is not electrically connected in the lead. Suture grooves are provided circumferentially around the sleeve in which the sutures are wrapped around. The flat wire and polymer covering are intended to stop the suture material from cutting through the sleeve body and into the medical lead, thereby causing damage to the lead.

Unlike the present invention, Helland does not disclose a spirally cut metal insert nor a flexible fiber mesh that is incorporated in the sleeve body to prevent lead damage.

Sommer et al. in U.S. Pat. No. 7,082,337 discloses a suture sleeve that comprises a hollow sleeve body with a sleeve insert that is covered with a layer of fibrous media. The suture sleeve of the '337 patent comprises a sleeve with an elastomeric insert designed with a rough surface that is embedded with a fibrous media of powder or grit of radiopaque metal, silica, ceramic or polymeric compound that is intended to prohibit physical damage to the lead.

Unlike the present invention, Sommer discloses a layer of particulate and fibrous material that surrounds the sleeve insert. This is distinctly different from the sleeve reinforcement embodiments of the present invention; specifically that of a fiber mesh that is embedded in the sleeve body itself. The design of the present invention provides a more robust barrier that protects the integrity of the suture sleeve and the medical lead. In addition, the fiber mesh embodiment of the present invention provides a degree of flexibility that allows the sleeve to bend with the lead which is not afforded by Sommer.

Therefore, what is needed is a flexible biocompatible reinforced suture sleeve that prevents damage to the implanted medical lead, suture material, as well as inhibits damage to the anchoring suture sleeve.

SUMMARY OF THE INVENTION

The present invention provides an improved reinforced suture sleeve that is designed to prohibit physical damage to an implanted medical lead. The reinforced suture sleeve of the present invention incorporates various physical barrier embodiments within the suture sleeve that minimize possible lead damage due to over tightening of the suture material. The present invention is comprised of two preferred suture sleeve reinforcement embodiments, both of which are designed to prevent damage to the lead as a result of propagation of the suture material into the medical lead.

The first suture sleeve reinforcement embodiment comprises a metallic insert that is preferably made of stainless steel or MP35N. The insert is tubular in shape with a length, a wall thickness, and a central throughbore that extends along a longitudinal axis of the insert, through the ends of the insert. The insert throughbore allows for the passage of a medical lead body through the insert. A slot, having a width and a length, is cut through the insert wall thickness in a spiral pattern along the insert's longitudinal length. The spiraled slot adds flexibility to the metallic insert by incorporating "spring-like" properties which enable the insert to bend and flex with the lead without any loss of structural integrity.

A polymer, preferably silicone, is molded over the insert to provide the body of the suture sleeve structure around which the suture material is wrapped. Grooves in the outside surface of the over molded polymer body provide a "track" to keep the suture material in place as it is wrapped circumferentially around the sleeve body.

In a second preferred suture reinforcement embodiment, the suture sleeve is designed with a fiber mesh that is embedded within the over-molded silicone sleeve body. The fiber mesh, which can be made of polymeric or metallic fibers, or combinations thereof, is incorporated within the polymeric sleeve body of the present invention. The fiber mesh provides a flexible barrier, within the sleeve body, that protects against suture line propagation. Thus, the integrity of the suture sleeve and medical lead is protected from potential damage due to an over tightened suture. In addition, the fiber mesh prevents the suture material from contacting the metal insert. Therefore, the possibility that the suture material will become damaged by abrading against the metal inert surface is minimized.

Additionally both reinforcement embodiments could be combined providing multiple barriers, both within the suture sleeve body and within the center of the sleeve that work in concert to provide complementary layers of protection.

DETAILED DESCRIPTION OF THE PREFERRED EMBODIMENTS

Figure 1:
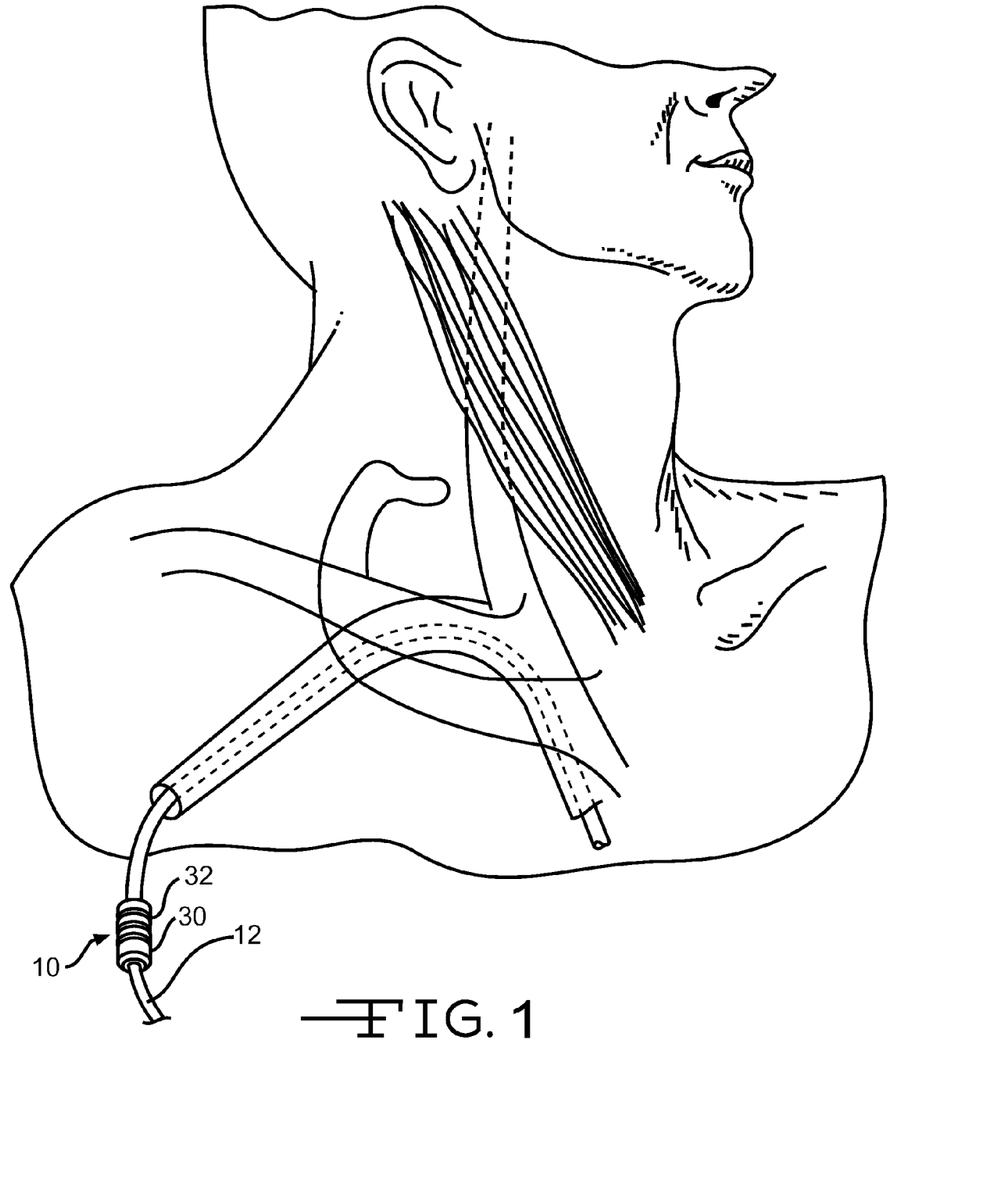
FIG. 1 shows a perspective view of an embodiment of the reinforced suture sleeve on a medical lead implanted in the body.

Now turning to the figures, FIG. 1 illustrates the reinforced suture sleeve 10 of the present invention, securing an implanted medical lead 12 in the body. As FIG. 1 shows, the medical lead 12 is positioned through the suture sleeve 10.

Figure 2:
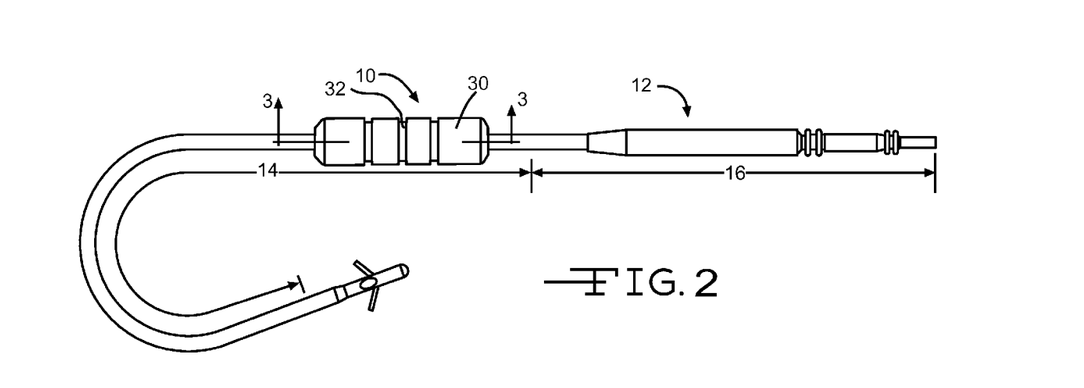
FIG. 2 shows a perspective view of an embodiment of the reinforced suture sleeve positioned on an implantable medical lead.

FIG. 2 depicts the suture sleeve 10 in place on the medical lead 12. The reinforced suture sleeve 10 of the present invention is properly positioned along the longitudinal axis A-A. As depicted in FIG. 2, the reinforced suture sleeve 10 of the present invention is shown positioned toward the lead distal region 14. The suture sleeve 10 is movable about the medical lead 12 and can be slid along the medical lead 12 to any desired location, such as the lead distal region 14 or the lead proximal region 16. The suture sleeve 10 is not limited to any one particular medical stimulation lead 12. The suture sleeve 10 can be used to secure and protect any style of medical lead 12 for use with a multitude of medical devices not limited to pacemakers, defibrillators, or neurostimulation devices.

Figure 3:
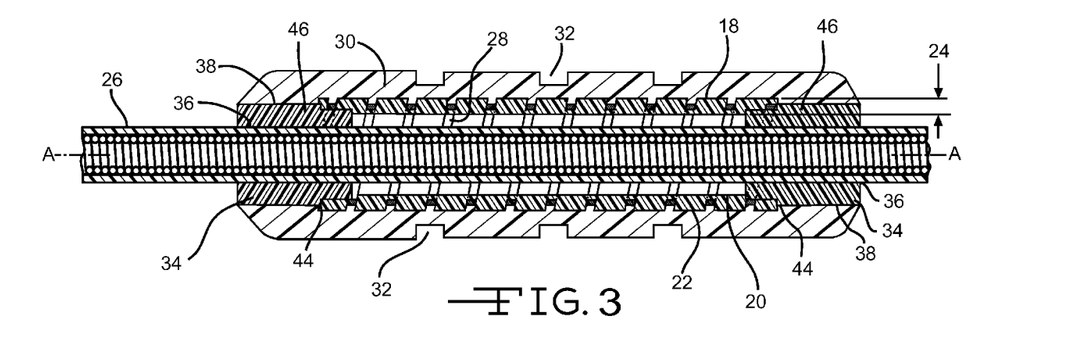
FIG. 3 illustrates an enlarged cross-sectional view taken along line 3-3, of the reinforced suture sleeve of the present invention.

FIG. 3 illustrates an enlarged cross-sectional view taken along line 3-3 of FIG. 2. depicting the internal structure of a preferred reinforcement embodiment of the suture sleeve 10 of the present invention. As the figure illustrates, the reinforced suture sleeve 10 extends circumferentially around the medical lead 12. The reinforced suture sleeve 10 is comprised of an internal insert 18 in which a pliable polymeric body is over molded.

The insert 18 is preferably tubular in shape with an inner insert wall surface 20, an external insert wall surface 22 and an insert wall thickness 24 therebetween. It is preferred that the insert 18 has an inner diameter of about 2.0 mm to about 4.0 mm and an external diameter of about 3.0 mm to about 5.0 mm resulting in a wall thickness 24 from about 1.0 mm to about 3.0 mm. The insert 18 has a preferred length of about 10.0 mm to about 30.0 mm which may or may not extend the entire length of the suture sleeve 10.

The insert 18 has a throughbore sized to allow the medical lead body 26 of a medical lead 12 to pass through. It is preferred that the insert 18 is made of a biocompatible metallic material, most preferably of stainless steel or MP35N. However, other biocompatible metallic materials could also be used.

At least one slot 28 is cut through the insert wall thickness 24 of the insert 18. The slot 28 has a width from about 0.2 mm to about 0.5 mm and is continuous along the longitudinal length (axis A-A) of the insert 18. The slot 28 is oriented in a spiral pattern such that the slot 28 extends along the longitudinal length of the insert 18 at a pitch angle from about 10 degrees to about 80 degrees relative to longitudinal axis A-A.

The position and pitch of the spiral pattern of the slot 28 is important to prevent the suture material from propagating through the insert 18 and into the medical lead 12. For example, the suture material is wrapped circumferentially around the polymeric body 30 within the boundaries of the suture groves 32 such that the suture material is perpendicular to the longitudinal axis A-A. In order for the suture material to cut through the polymeric body 30, it must propagate through the polymeric body 30 perpendicularly to the longitudinal axis A-A.

The metallic insert 18 blocks the progress of the sutures as it cuts perpendicularly through the polymeric body 30. The spiraled orientation of the slot 28 is positioned such that the pitch of the slot 28 prevents the suture material from sliding between the width of the slot 28, therefore protecting the medical lead 12 from damage. The spiral pattern of the slot 28 through the wall of the insert 24 adds flexibility and allows the insert 18 to bend easily. Without the spiraled slot 28, the solid metallic insert 18 would be incapable of bending.

A polymeric body 30 is molded over the circumference of the insert 18, encompassing the insert 18 within. The polymeric body 30 is molded around the insert 18 such that the tubular ends of the insert 18 are open. The polymeric body 30 is preferably made from a pliable polymer material, most preferably of silicone. A series of at least two suture grooves 32 are cut into the outer surface of the polymeric body 30. These suture grooves 32 circumferentially extend around the polymeric body 30, keeping the sutures in a perpendicular orientation with respect to the longitudinal axis A-A. In a preferred embodiment, each suture groove 32 has a depth of about 0.3 mm to about 0.5 mm and a width of about 0.5 mm to about 1.0 mm.

An end tube 34 is inserted into the opposite ends of each insert 18. Each tube 34 has a circular diameter, and a tube length of about 2.0 mm to about 3.5 mm. Each tube 34 has an inner tube wall surface 36, a tube outer wall surface 38, a tube thickness therebetween 40, and a tube throughbore 42 extending through the longitudinal length of each tube 34. The tube throughbore 42 is sized to allow the passage of a medical lead 12 through the tube 34. The tube 34 is formed as such that a frictional fit between the medical lead body 26, and the inner tube wall surface 36 as shown in FIG. 3, is created. Each tube 34 is preferably made of a pliable polymeric material, most preferably, silicone.

Each end tube 34 has a step 44 in which the outer diameter abruptly decreases to a smaller diameter at a tube distal end 46. This step 44 enables the tube 34 to fit into each end of the insert 18. The tube distal end 46 is sized to fit snuggly beneath the inner insert wall surface 20. The tube outer wall surface 38 and the suture sleeve inner wall surface 48 form a frictional fit therebetween as each tube 34 is inserted into the opposite ends of the insert 18.

The inner tube wall surface 36 provides sufficient friction to prevent the reinforced suture sleeve 10 from sliding down the medical lead body 26 under the force of gravity alone. Once the reinforced suture sleeve 10 is in place, it must be repositioned by physically sliding the sleeve 10 along the medical lead body 26.

Figure 4:
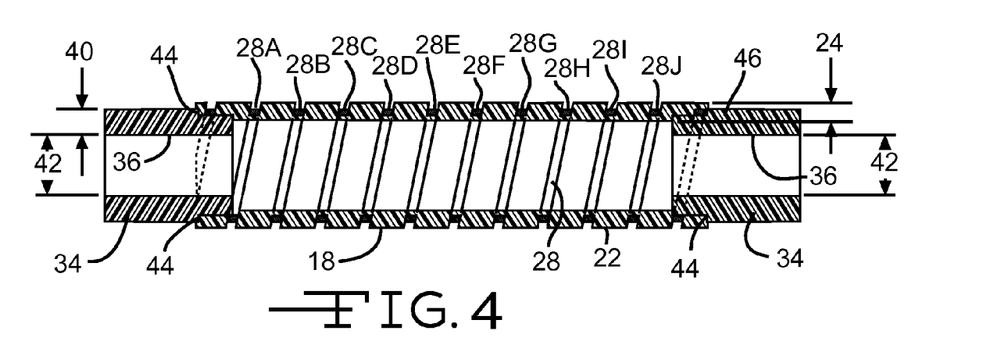
FIG. 4 is a cross-sectional view depicting the metallic insert of the reinforced suture sleeve during an intermediate manufacturing process step.
Figure 5:
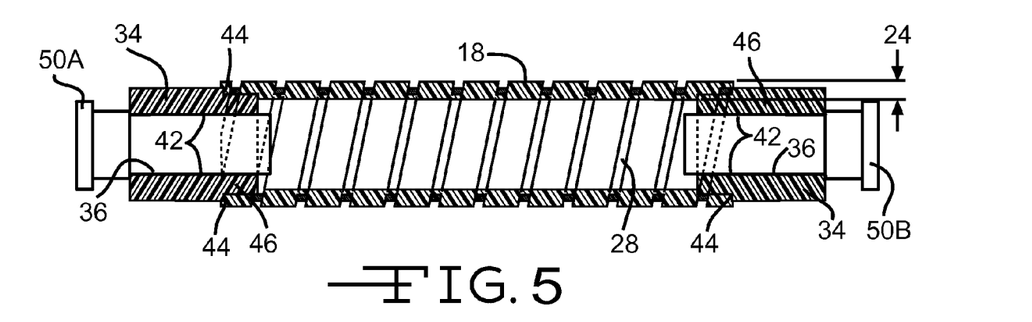
FIG. 5 illustrates a cross-sectional view depicting the metallic insert of the reinforced suture sleeve during an intermediate manufacturing process step.
Figure 6:
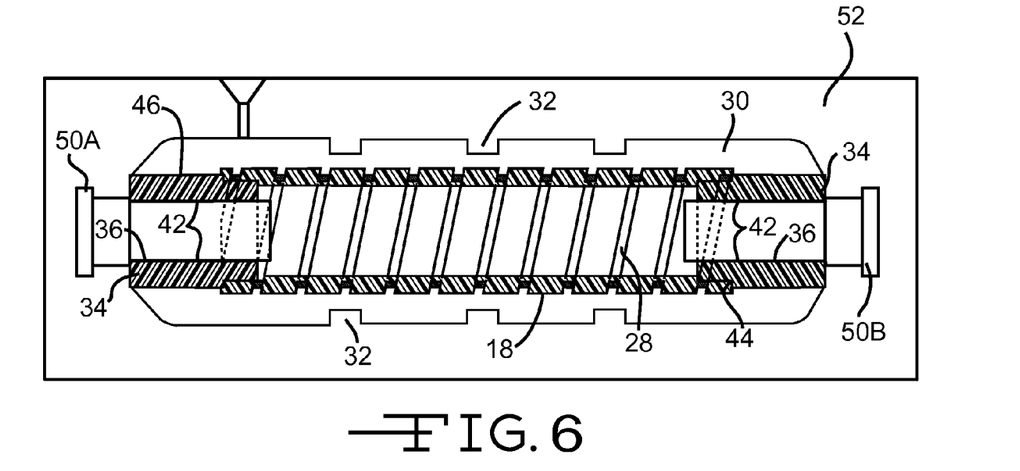
FIG. 6 depicts a cross-sectional view showing the metallic insert of the present invention placed into a mold.

FIGS. 4, 5, and 6, illustrate the steps of manufacturing the reinforced suture sleeve 10 of the present invention. In the first step of the manufacturing process, a tubular insert 18 is provided. A laser is preferably used to spirally cut the slot 28 through the insert wall thickness 24. FIG. 4 illustrates the angled groove of the slot 28 as it is spirally cut around the longitudinal length of the insert 18. These angled grooves are shown as 28A, 28B, 28C, 28D 28E, 28F, 28G, 28H, 28I, and 28J in this cross-sectional view.

Alternatively, an alternate cutting device, not limited to a water mill, torch or band saw could also be used to cut the spiral pattern slot 28 through the surface of the insert 18 around the longitudinal length of the insert 18.

Once the insert 18 has been cut, an end tube 34 is fitted into each of the opposite ends of the insert 18. FIG. 4 illustrates the insert 18 fitted with a tube 34 that has been inserted into the respective opposite ends of the insert 18.

Once the end tubes 34 have been inserted into the ends of the insert 18, mandrels 50A, 50B are then placed into the end of each tube 34. These mandrels 50 are temporarily inserted into the ends of each tube 34 during the molding process to prevent the molding material from entering through the ends of the tube throughbore 42 and thus into the insert 18. It is not desirable for the molding material to enter inside of the insert 18. If the molding material were to enter inside the insert 18, the passage of the medical lead 12 through the suture sleeve 10 would be impeded. FIG. 5 illustrates this intermediate assembly comprising the insert 18, tubes 34 and mandrels 50A, 50B. The insert 18 is now ready for the polymeric body 30 to be molded over the intermediate assembly of the insert 18 and end tubes 34 as shown in FIG. 5.

Figure 7:
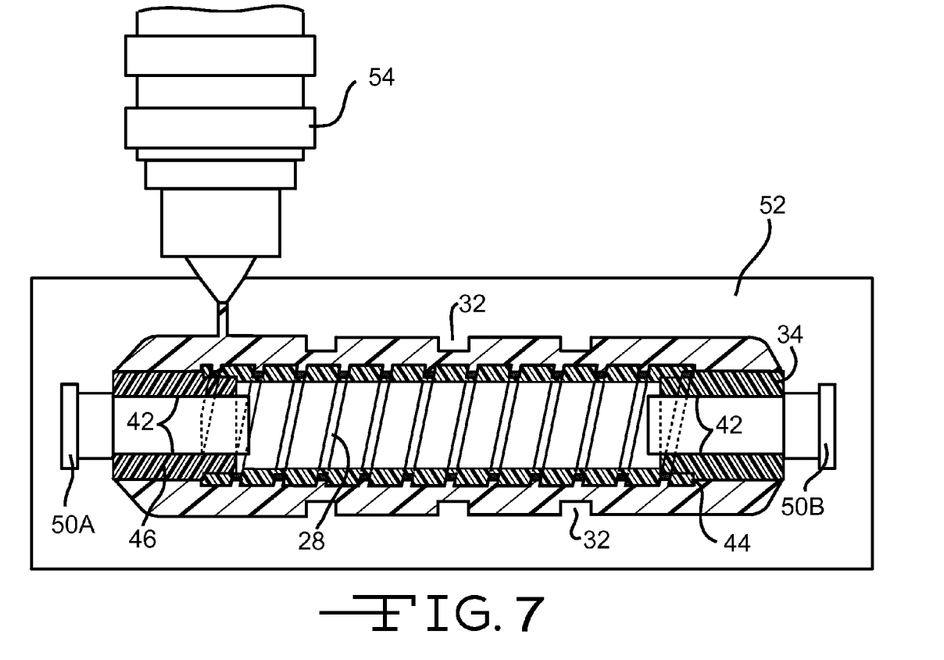
FIG. 7 is a cross-sectional view illustrating a polymeric material being molded over the insert.

As shown in FIG. 6, the intermediate assembly comprising the insert 18, end tubes 34, and mandrel ends 50A,50B is then placed in a mold 52 to form the suture sleeve body 30. A mold head 54, as shown in FIG. 7, is then attached to the mold 52 and the molding material, preferably silicone, is flowed through the mold head 54 into the mold 52, forming the body 30 around the intermediate assembly of the insert 18 and end tubes 34. Once the over molding process is complete, the mandrel ends 50A,50B are removed and the finished reinforced suture sleeve 10 is removed from the mold 52.

Figure 8:
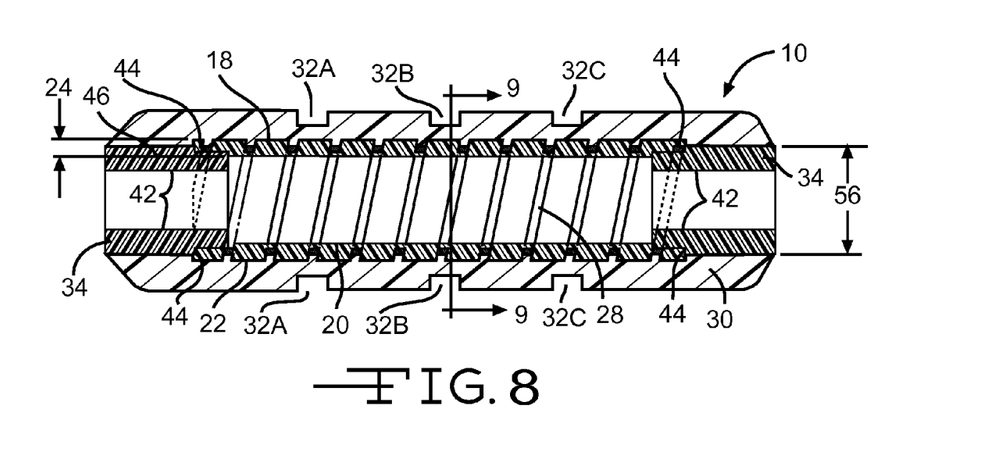
FIG. 8 illustrates a cross-sectional view of a completed reinforced suture sleeve of the present invention.

FIG. 8 illustrates a cross-sectional view of the completed reinforced suture sleeve 10 of the present invention. As the illustration depicts, the polymeric body 30 is over molded over the insert 18 and end tubes 34 forming a sealed, durable and flexible reinforced sealed suture sleeve 10. As the figure shows, the reinforced suture sleeve 10 has a hollow passageway or sleeve throughbore 56 that extends within the suture sleeve 10 in which a medical lead 12 is passed through. The opening of the internal suture sleeve hollow passageway 56 is constricted by the tube throughbore opening 42 which forms a frictional fit against the medical lead body 26.

Figure 9:
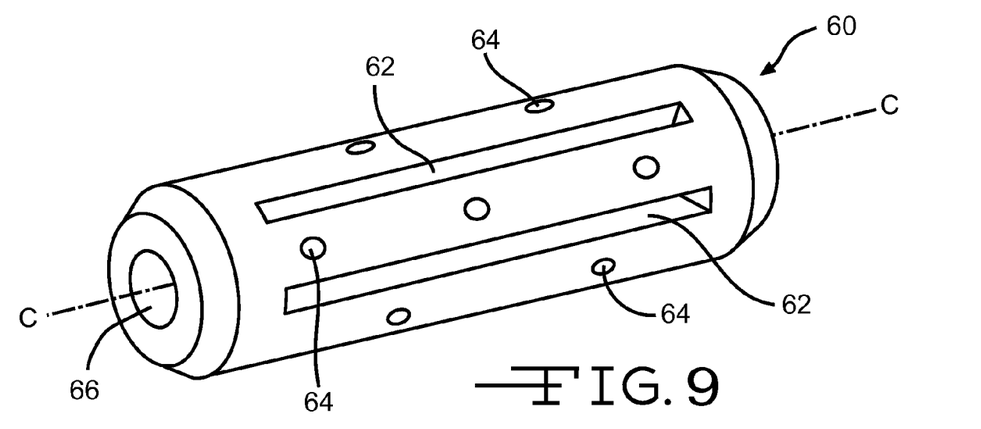
FIG. 9 depicts a perspective view of an alternate embodiment of a metallic insert of the present invention.

FIG. 9 depicts an alternate embodiment of an insert 60 according to the present invention. As the illustration shows, the alternate insert 60 has a tubular shape with an insert outer diameter from about 3.0 mm to about 5.0 mm and an insert length from about 15.0 mm to about 20.0 mm. Insert 60 has a series of longitudinal slots 62 extending along longitudinal axis C-C. Each slot 62 has a length from about 15.0 mm to about 20.0 mm and a width from about 0.5 mm to about 1.0 mm. As shown, insert 60 has a plurality of spaced apart indents 64. These indents 64 are designed to increase the robustness of the seal between the insert 60 and the polymeric sleeve 30.

The insert 60 as shown in FIG. 9, has an opening 66 with a diameter of about 2.0 mm to about 4.0 mm. Opening 66 is sized such that a medical lead 12 can pass through.

The insert 60 is encompassed in a polymeric body 30 in the over-molding process that was previously described.

Figure 10:
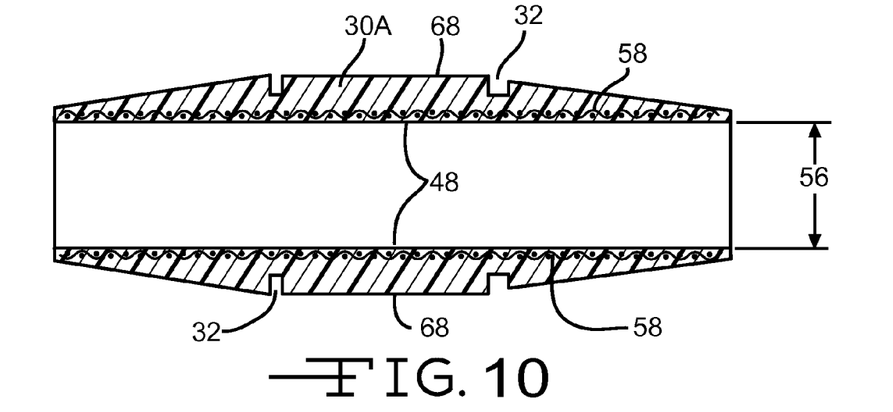
FIG. 10 depicts a cross-sectional view illustrating an alternate reinforcement embodiment of a polymeric body 30A.
Figure 11:
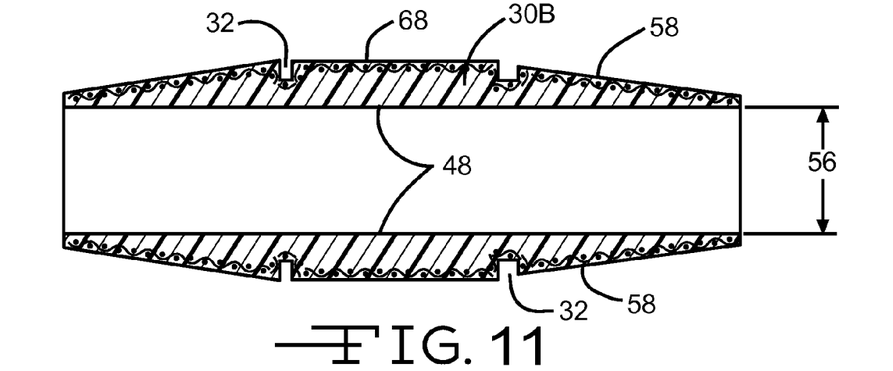
FIG. 11 depicts a cross-sectional view illustrating an alternate reinforcement embodiment of a polymeric body 30B.

In an alternate embodiment, the suture sleeve 10 can also be reinforced with the addition of a fiber mesh 58 that is embedded within the polymeric body 30, as shown in FIGS. 10 and 11. In this alternatively preferred embodiment, a fiber mesh 58 comprising flexible metallic or polymeric fibers or combinations thereof, is incorporated into the internal structure of the molded body 30. It is more preferred that the fiber mesh 58 be made of a polymeric fiber mesh material such as polyethylene terephthalate), which is a material manufactured under the trade name of Dacron®. In so doing, the suture sleeve 10 is reinforced within the polymeric body 30. Therefore the suture material is prevented from cutting through the body 30 before the sutures reach the insert 18.

FIG. 10 depicts a preferred alternate polymeric body 30 embodiment in which a fiber mesh 58 is embedded into the structure of the body. As the figure illustrates, the fiber mesh 58 is embedded within the body inner wall surface 48. Therefore, a barrier is created that prevents sutures from cutting through the insert 18 and into the lead body 26. Alternatively, the fiber mesh 58 can be embedded within the outer wall surface 68 of the polymeric body, as shown in FIG. 11. Additionally, the placement of the fiber mesh 58 is not limited to being positioned at the inner wall surface 48 or the suture outer wall surface 68. Instead it could be placed in both locations or throughout the structure of the body 30. For example, the embedded fiber mesh 58 could be disposed proximate an outer surface of the polymeric body 30B or be disposed proximate an inner surface of the polymeric body 30A. The placement of the fiber mesh 58 at the outer wall surface 68 prohibits the suture material from cutting into the polymeric body 30.

In addition to protecting the medical lead 12, the embedded fiber mesh 58 prevents the suture material from contacting the metal insert 18, thereby protecting the suture material from damage. The fiber mesh 58 acts as a barrier that prevents the suture material from contacting and abrading against the surface of the metal insert 18. Therefore, the anchoring suture material is kept intact, preventing the suture sleeve 10 from becoming detached from the surrounding tissue to which it is anchored.

It is contemplated that both reinforcement embodiments could be combined into one reinforced suture sleeve 10. Therefore a suture sleeve 10 is created in which a spiraled cut metallic insert 18 and fiber mesh 58 are both combined into one reinforced suture sleeve 10 in a separate embodiment.

Figure 12:
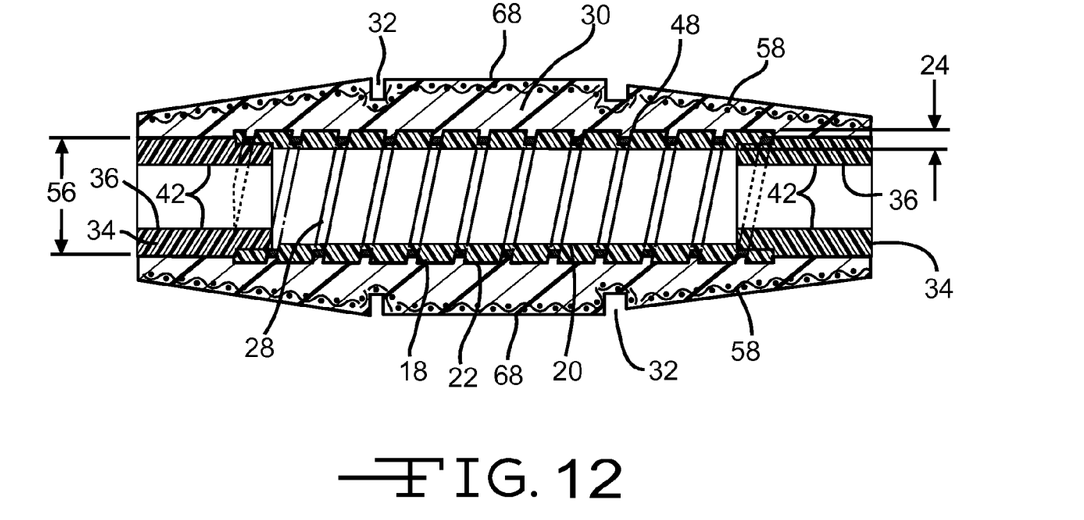
FIG. 12 shows a cross-sectional view illustrating an alternate reinforced suture sleeve embodiment according to the present invention.

FIG. 12 illustrates such an embodiment in which a reinforced suture sleeve 10 is comprised of a spiraled cut metallic insert 18 and a polymeric body 30 that is provided with a fiber mesh 58. Therefore, by combining the two reinforcement embodiments, a flexible, durable suture sleeve 10 is created that provides two layers of protection from the damaging effects of an over tightened sutures. The first layer of protection is located in the polymeric body 30 with the second layer of protection being the spirally cut insert 18.

Therefore, the present suture sleeve invention embodies multiple reinforcement embodiments that provide superior protection from over tightened sutures.

What is claimed is:

1. A suture sleeve comprising:
   a) a tubular insert comprising an annular insert sidewall having an insert length and defining an insert throughbore extending along a longitudinal axis between and to spaced apart first and second open insert ends, wherein the insert sidewall has an insert thickness extending from an inner annular insert surface to an outer annular insert surface;
   b) at least one slot extending part-way into the insert sidewall from the outer insert surface thereof to thereby provide a slot depth that is less than the insert thickness with the inner insert surface being uninterrupted by the slot, wherein the slot has a spiral pattern extending around the insert sidewall and axially along the longitudinal axis at least part-way along the insert length;
   c) first and second tubes, each tube comprising a tube sidewall having a tube length that is partially received within a respective one of the first and second open insert ends to thereby provide a received portion of each of the first and second tube lengths, the received portions having respective received lengths that together are less than the insert length, wherein the first and second tubes each define a tube throughbore that is in open communication with the insert throughbore, and
   d) wherein an inner tube diameter at the respective first and second tube throughbores is less than an inner insert diameter at the insert throughbore to thereby provide respective steps from the inner tube diameter of the first and second tubes outwardly to the inner insert diameter so that the insert throughbore is constricted by the first and second tube throughbores; and
   e) a polymeric body encasing at least part of the outer insert surface including the slot and encasing at least part of the first and second tubes other than their respective received portions where the first and second tubes are received in the respective first and second open insert ends.

2. The suture sleeve of claim 1 wherein the slot has a pitch from about 10 degrees to about 80 degrees with respect to the longitudinal axis.

3. The suture sleeve of claim 1 wherein the insert is of a metallic material.

4. The suture sleeve of claim 1 wherein the insert is of stainless steel or MP35N.

5. The suture sleeve of claim 1 wherein the polymeric body is of a biocompatible polymer.

6. The suture sleeve of claim 1 wherein the polymeric body is of silicone.

7. The suture sleeve of claim 1 wherein a fiber mesh is embedded within the polymeric body.

8. The suture sleeve of claim 7 wherein the fiber mesh is selected from the group consisting of polymer fibers, metallic fibers, and combinations thereof.

9. The suture sleeve of claim 7 wherein the fiber mesh is disposed proximate an outer surface of the polymeric body.

10. The suture sleeve of claim 7 wherein the fiber mesh is disposed proximate an inner surface of the polymeric body.

11. The suture sleeve of claim 1 wherein at least one indent extends part-way into the insert thickness from the outer insert surface.

12. The suture sleeve of claim 1 wherein the polymeric body comprises an intermediate body portion extending to opposed first and second tapered body end portions, and wherein the intermediate body portion has an outer intermediate body surface, and wherein each of the first and second tapered polymeric body end portions tapers downwardly and inwardly along the longitudinal axis from the outer intermediate body surface to respective first and second polymeric body end surfaces that are spaced from, but aligned substantially perpendicular to the longitudinal axis.

13. The suture sleeve of claim 12 wherein a suture groove extends from the outer intermediate polymeric body surface part-way through a thickness of the polymeric body.

14. The suture sleeve of claim 1 wherein the first and second tubes each have a distal tube end surface spaced from the insert throughbore.

15. A method for manufacturing a suture sleeve, comprising the following steps:
 a) providing a tubular insert comprising an annular insert sidewall having an insert length and defining an insert throughbore extending along a longitudinal axis between and to spaced apart first and second open insert ends, wherein the insert sidewall has an insert thickness extending from an inner annular insert surface to an outer annular insert surface; and
 b) forming at least one slot extending part-way into the insert sidewall from the outer insert surface thereof to thereby provide a slot depth that is less than the insert thickness with the inner insert surface being uninterrupted by the slot, wherein the slot has a spiral pattern extending around the insert sidewall and axially along the longitudinal axis at least part-way along the insert length;
 c) providing first and second tubes, each tube comprising a tube sidewall having a tube length;
 d) partially positioning one of the first and second tubes within a respective one of the first and second open insert ends to thereby provide a received portion of each of the first and second tube lengths, the received portions having respective received lengths that together are less than the insert length, wherein the first and second tubes each define a tube throughbore that is in open communication with the insert throughbore, and wherein an inner tube diameter at the respective first and second tube throughbores is less than an inner insert diameter at the insert throughbore to thereby provide respective steps from the inner tube diameter of the first and second tubes outwardly to the inner insert diameter so that the insert throughbore is constricted by the first and second tube throughbores; and
 e) molding a polymeric body encasing at least part of the outer insert surface including the slot and encasing at least part of the first and second tubes other than their respective received portions where the first and second tubes are received in the respective first and second open insert ends.

16. The method of claim 15 including forming the at least one slot in a spiral pattern having a pitch angle of about 10 degrees to about 80 degrees with respect to the longitudinal axis.

17. The method of claim 15 wherein the polymeric body is made of silicone.

18. The method of claim 15 including embedding a fiber mesh in the polymeric body.

19. The method of claim 18 including selecting the fabric mesh from the group consisting of polymeric fibers, metallic fibers, and combinations thereof.

20. The method of claim 18 including embedding the fiber mesh more proximate an outer surface of the polymeric body than an inner polymeric surface contacting the outer insert surface and an outer tube surface.

21. The method of claim 15 including providing at least one indent extending part-way into the insert thickness from the outer insert surface.

22. A suture sleeve comprising:
 a) a tubular insert comprising an annular insert sidewall having an insert length and defining an insert throughbore extending along a longitudinal axis between and to spaced apart first and second open insert ends, wherein the insert sidewall has an insert thickness extending from an inner annular insert surface to an outer annular insert surface;
 b) at least one slot extending part-way into the insert sidewall from the outer insert surface thereof to thereby provide a slot depth that is less than the insert thickness with the inner insert surface being uninterrupted by the slot, wherein the slot has a spiral pattern extending around the insert sidewall and axially along the longitudinal axis at least part-way along the insert length;
 c) first and second tubes, each comprising a tube sidewall having a tube length that is partially received within a respective one of the first and second open insert ends to thereby provide a received portion of each of the first and second tube lengths, the received portions having respective received lengths that together are less than the insert length, wherein the first and second tubes each define a tube throughbore that is in open communication with the insert throughbore, and
 d) wherein an inner tube diameter at the respective first and second tube throughbores is less than an inner insert diameter at the insert throughbore to thereby provide respective steps from the inner tube diameter of the first and second tubes outwardly to the inner insert diameter so that the insert throughbore is constricted by the first and second tube throughbores; and
 e) a polymeric body encasing the outer insert surface including the slot and encasing at least part of the first and second tubes other than their respective received portions where the first and second tubes are received in the respective first and second open insert ends, wherein the polymeric body comprises an intermediate body portion extending to opposed first and second tapered body end portions, and wherein the intermediate body portion has an outer intermediate body surface, and wherein each of the first and second tapered polymeric body end portions tapers downwardly and inwardly along the longitudinal axis from the outer intermediate body surface to respective first and second polymeric body end surfaces.

23. The suture sleeve of claim 22 wherein the first and second tubes each have a distal tube end surface spaced from the insert throughbore.

24. The suture sleeve of claim 22 wherein the distal first and second tube end surfaces are co-planar with the respective first and second body end surfaces of the polymeric body.

25. The suture sleeve of claim 22 wherein the first and second polymeric body end surfaces are spaced from, but aligned substantially perpendicular to the longitudinal axis.

\* \* \* \* \*